United States Patent [19]
Sashin et al.

[11] Patent Number: 6,138,302
[45] Date of Patent: Oct. 31, 2000

[54] APPARATUS AND METHOD FOR POSITIONING PATIENT

[75] Inventors: Donald Sashin; Brian J. Lopresti, both of Pittsburgh, Pa.

[73] Assignee: University of Pittsburgh of The Commonwealth System of Higher Education, Pittsburgh, Pa.

[21] Appl. No.: 09/189,264

[22] Filed: Nov. 10, 1998

[51] Int. Cl.[7] .................................................... A61B 5/00
[52] U.S. Cl. ........................... 5/600; 5/601; 5/621; 5/622
[58] Field of Search ................................. 5/601, 621, 622, 5/637, 600; 128/845, 846; 378/20, 68, 177, 195, 208

[56] References Cited

U.S. PATENT DOCUMENTS

| | | |
|---|---|---|
| 4,616,814 | 10/1986 | Harwood-Nash et al. .............. 5/622 X |
| 5,315,630 | 5/1994 | Sturm et al. ............................... 378/65 |
| 5,370,117 | 12/1994 | McLaurin ..................................... 5/622 |
| 5,588,430 | 12/1996 | Bova et al. . |
| 5,807,255 | 9/1998 | Yokota et al. ............................... 5/622 |
| 5,823,192 | 10/1998 | Kalend et al. . |
| 5,829,444 | 11/1998 | Ferre et al. . |

OTHER PUBLICATIONS

Polaris Optical Tracking System Instruction Manual NDI–IM Polaris Rev. 002, Published by Northern Digital Inc., Copyright 1996, pp. 1–16.

Primary Examiner—Lynne H. Browne
Assistant Examiner—Fredrick Conley
Attorney, Agent, or Firm—Arnold B. Silverman; Brij K. Agarwal; Eckert Seamans Cherin & Mellott, LLC

[57] ABSTRACT

Apparatus is disclosed for maintaining the position of a patient during a medical procedure such as imaging by position emission tomography (PET) or magnetic resonance imaging (MRI) or radiotherapeutic uses of medical procedures wherein maintaining a portion of the patient's body in a stationary position is important. The apparatus includes a system for tracking motion of the particular body portion of interest, such as the head, a computer for receiving signals from the tracking system, and determining if undesired motion of the body portion has occurred and, if so, issuing a corrective signal which through a plurality of motors effects repositioning of the body portion to the desired location. This monitoring and repositioning may take place at a very high frequency. A particular contemplated use is immobilizing and positioning of the head during brain scans. An associated method is disclosed.

26 Claims, 12 Drawing Sheets

APPARATUS AND METHOD FOR POSITIONING PATIENT

BACKGROUND OF THE INVENTION

1. Field of the Invention

The present invention relates to apparatus and an associated method for facilitating positioning of a patient in such a manner as to maximize the efficiency of the patient's imaging and/or therapeutic procedures and, more specifically, the invention is directed toward a system which automatically repositions a portion of a patient's body which is of interest and has moved during a medical procedure.

2. Description of the Prior Art

It has long been known that for various forms of diagnostic imaging, as well as radiotherapy, that proper immobilization of the portion of the patient's body being imaged or treated will contribute meaningfully to the clarity and resolution of image and efficiency of therapy. With respect to the use of x-rays as in x-ray computed tomography, purely anatomical information is obtained at a very rapid rate.

With respect to improved technology such as that used in positron emission tomography (PET), magnetic resonance imaging (MRI), or radiotherapy may require immobilizing the portion of the patient's body for periods of from 10 seconds to 20 minutes. Motion of the patient body portion of interest during this period can cloud the image and interfere with efficiency of therapy. Among the advantages of PET is the ability to obtain functional information regarding a portion of the patient's body, such as the brain.

In PET, radiotracers which are designed to be substrates for various biological processes, may be injected into the body. These compounds can be constructed around a cyclotron-produced positron-emitting nuclide of a biologically occurring element such as $^{11}C$, $^{5}O$ and $^{18}F$. By way of a specific example, the PET radiotracer [$^{18}F$]2-fluoro-2-deoxyglucose (FDG)] is a known substrate for energy metabolism. FDG can be used to locate small cancerous tumors throughout the body as well as to assess stroke damage to the brain.

Specific PET radiotracers have been developed in recent years to image complex aspects of brain function which may be used in the diagnosis and study of serious neurodegenerative and neuropsychiatric illnesses, such as Alzheimer's Disease, Schizophrenia and Parkinson's Disease. PET studies have also been useful tools in mapping functional organization of the normal human brain.

PET cameras are now capable of imaging a 20 cm or larger axial field of view in three dimension with a spatial resolution of less than 2.0 mm. As increased efforts are made to study smaller and smaller structures within the brain, movement of the patient's head during such studies contributes more significantly to reduction in resolution and the presence of undesirable movement artifacts. Similar problems exist in respect of magnetic resonance imaging (MRI) which may have a spatial resolution greater than an order of magnitude larger than PET.

It has been known to reduce patient head movement and the accompanying blurring of image and loss of contrast and resolution by providing a head support underlying the patient and a thermoplastic face mask which is molded to the patient's head and secured to the head support.

It has been suggested to employ optical tracking systems to monitor such movement and to attempt to correct the variations in data due to undesired patient movement.

There remains, therefore, a very substantial need for improved means of minimizing the detrimental effect on diagnostic and therapeutic procedures resulting from undesired patient movement.

SUMMARY OF THE INVENTION

The present invention has met the above-described needs by providing a system for monitoring patient movement with great frequency and if the body portion of interest, such as the head moves in an undesired manner, effecting immediate correction of the same.

The apparatus for positioning a patient includes means for restraining the portion of the patient's body being subjected to a medical procedure, which may be diagnostic or therapeutic, tracking means for tracking motion of the body portion, and computer means for receiving signals from the tracking means and determining if the body portion has moved from the desired position and, if so, emitting a corrective signal to power means. The power means responsive to the computer means corrective signal moves the body portion back to the desired position.

In a preferred embodiment, the power means includes six motors with three being positioned perpendicular with respect to each other along orthogonal axes and the other three motors serving to effect rotational movement of the head support about the orthogonal axes. By employing one or more of these translational and rotational movement capabilities, the original head position may be restored.

In an associated method the portion of the patient's body which is said to be subjected to a medical procedure is restrained as by placing the same on a head support with a mask overlying the face being secured to the head support. The motion of the body portion is tracked and responsive to computer signals indicating that movement has occurred, the motors move the patient body portion to the desired position.

It is an object of the present invention to provide a system for positioning a patient for diagnostic or therapeutic procedures such that the detrimental effect of patient movement can be minimized.

It is a further object of the present invention to provide such apparatus and method which is adapted to support the patient's head in a particular position and restore the patient to substantially the original position if undesired head movement has occurred.

It is a further object of the present invention to provide such a system which permits improved contrast sensitivity and resolution of positron emission tomography (PET) and functional MRI imaging studies, as well as improving therapy, such as radiotherapy treatment.

It is a further object of the present invention to provide such a system which is economical to manufacture and operate and is compatible with existing medical imaging and radiotherapy equipment and procedures.

It is a further object of the present invention to provide such a system which can employ conventional head restraints and resist increased patient anxiety or physical discomfort.

It is a further object of the present invention to provide such a system which is servo driven and can compensate for even very small movements of the head and reposition the head promptly to its original position.

These and other objects of the invention will be more fully understood from the following description of the invention on reference to the illustrations appended hereto.

DESCRIPTION OF THE PREFERRED EMBODIMENTS

As used herein, the term "patient" shall mean members of the animal kingdom, including human beings and inanimate objects.

The term "medical procedure" as used herein shall mean a diagnostic imaging procedure, functional imaging study, imaging of an animal or imaging of an object, or a radiotherapy procedure.

The term "motor" as employed herein shall include electrically energized motors, stepping motors, hydraulic cylinders, pneumatic cylinders, as well as other motors which are adapted to rotate in either direction and produce responsive (a) rotary output or (b) linear output in either direction. It shall also expressly include any such actuator which produce linear movement of an element responsive to rotation of a threaded output shaft within a threaded bore which is operatively associated with or integrally formed a slide element.

Figure 1:
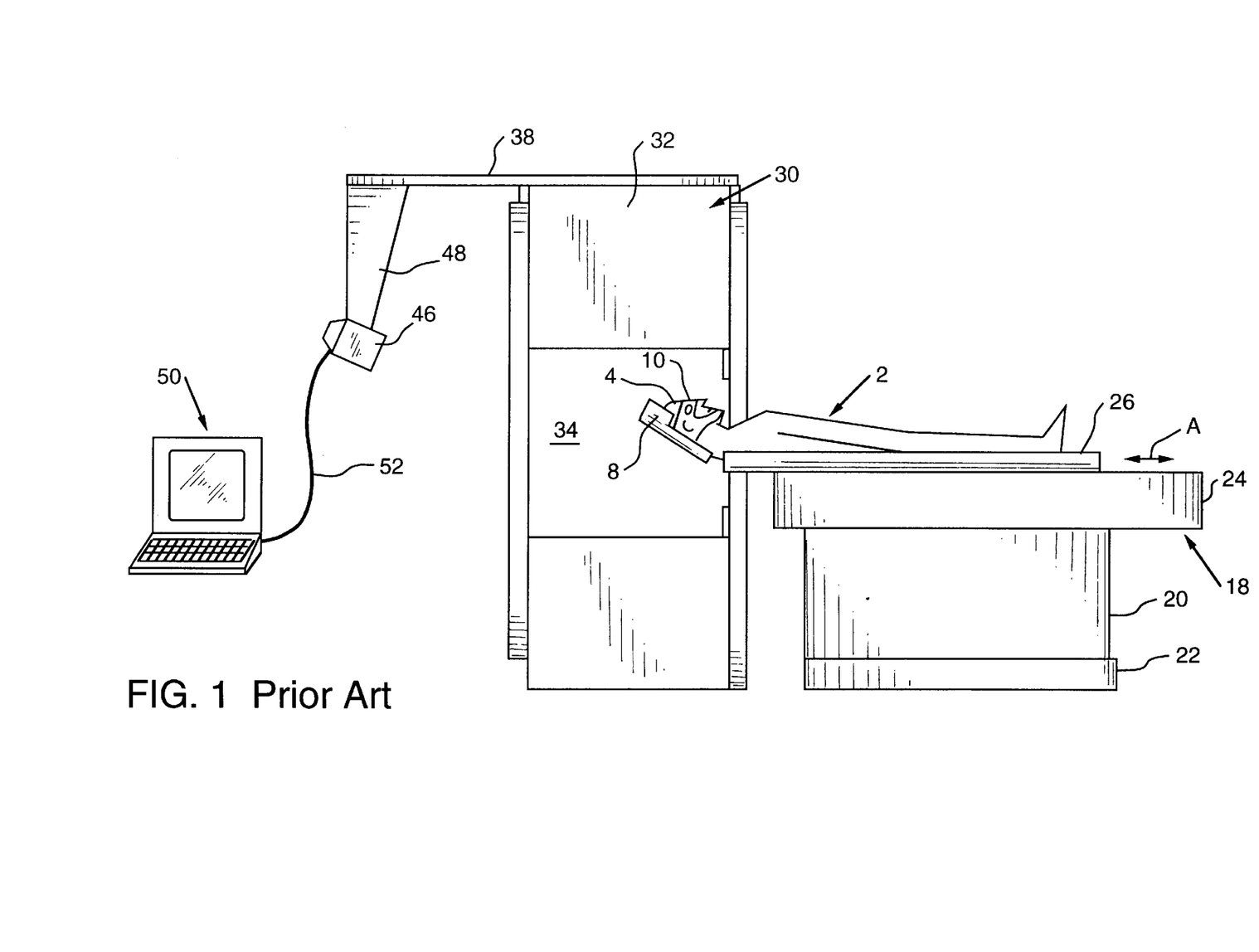
FIG. 1 is schematic elevational view showing a prior art motion tracking system and associated computer unit for use with a PET system.

Referring to FIG. 1, a prior art system for PET medical procedures not involving repositioning of the body portion which, in the form shown is a head, will be considered. In this apparatus and the associated procedure, a patient 2 has his or her head 4 supported by a head support 8 which underlies the head 4. A custom-created face mask 10 is secured over the patient's face and is secured by means (not shown) to the underlying head support 8. The apparatus has a bed 18 which rests on a suitable support 20 which, in turn, rests on a base 22. The upper portion of the bed 24 contains suitable tracks (not shown) to permit the patient supporting part 26 of the bed 24 to be subjected to relative movement in the direction indicated by two-headed arrow A. The PET scanner 30 has its scanning equipment disposed in annular portion 32 which defines patient receiving tunnel 34. Gantry 38 supports position sensor 46 by means of connecting arm 48. The position sensor 46 is preferably an optical tracking system which shines light on reflectors (not shown in this view) positioned on the top of the patient's head and monitors movement by the position of the reflected light received by the position sensor 46. A computer 50 is connected to the position scanner 46 by interface 52. The information received in the computer may, in association with the hardware, interfaces, and software provide desired information regarding patient head movement.

Figure 2:
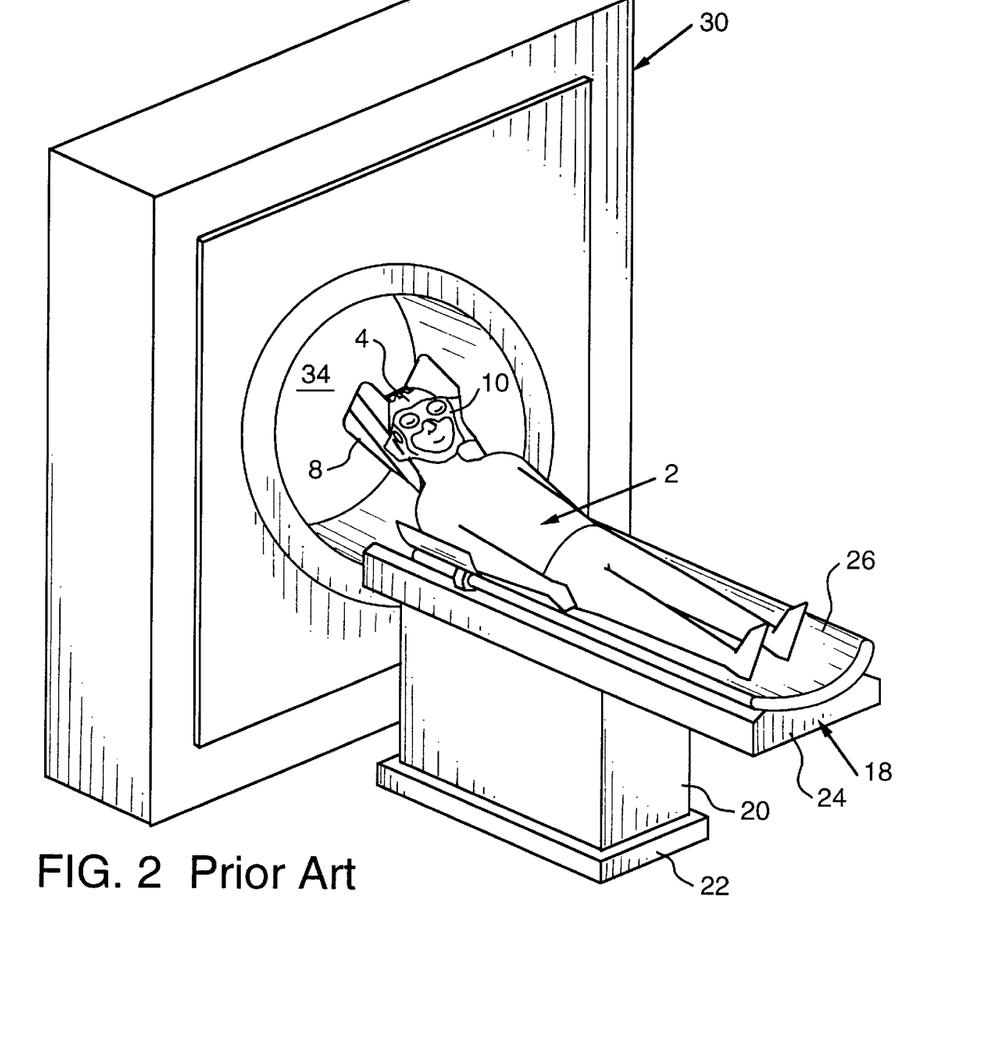
FIG. 2 is a partially schematic perspective view showing a patient on a movable bed and the associated prior art imaging apparatus for use with imaging or radiotherapy treatment of a patient's head.

FIG. 2 shows the system of FIG. 1 without the optical tracker system and illustrates it from the patient entry end of the tunnel.

Figure 3:
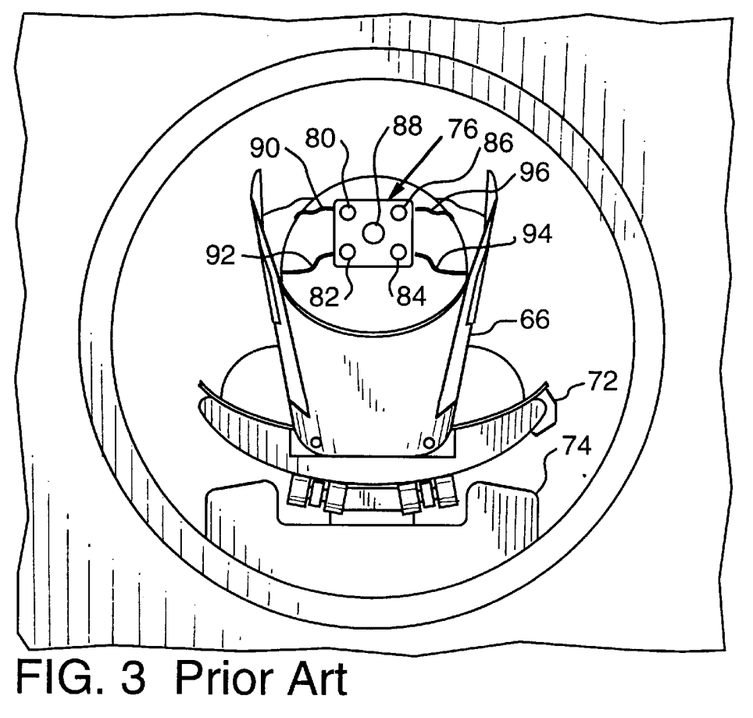
FIG. 3 is a rear elevational view showing a portion of the tunnel and the patient's head in a restrained position along with reflective elements for a prior art optical tracking system.
Figure 4:
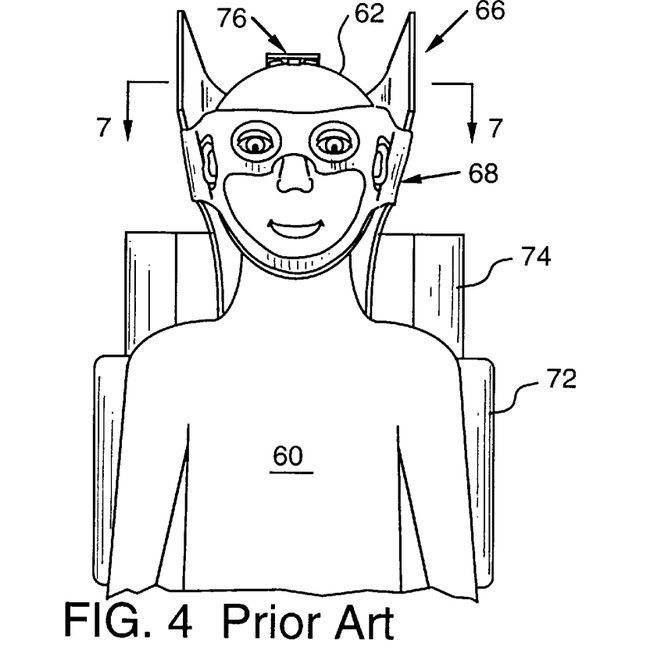
FIG. 4 is a top plan view showing the patient having the head restrained in accordance with prior art systems.

Referring to FIGS. 3 and 4, details of certain aspects of prior art use of diagnostic or therapeutic imaging or treatment of the brain with the head immobilized are illustrated. The patient 60 has his head 62 immobilized between an underlying substantially rigid upwardly open head support 66 and an overlying mask 68 which is secured to lateral portions of the head support 66. The patient is supported on the movable table portion 72 which is supported on a table portion 74. The reflector 76 is secured to the top of the patient's head and has a plurality of reflector elements 80, 82, 84, 86 and, in the form shown, a central opening 88. As light from the position sensor impinges on the head, reflectors 80, 82, 84, 86 reflect the light back to the position sensor. Any change in position of the head 62 results in a change in the reflected light thereby enabling the computer to calculate the magnitude and direction of head movement. Means for retaining the reflector 76 in intimate contact with the head are shown schematically by elongated members 90, 92, 94, 96.

Figure 5:
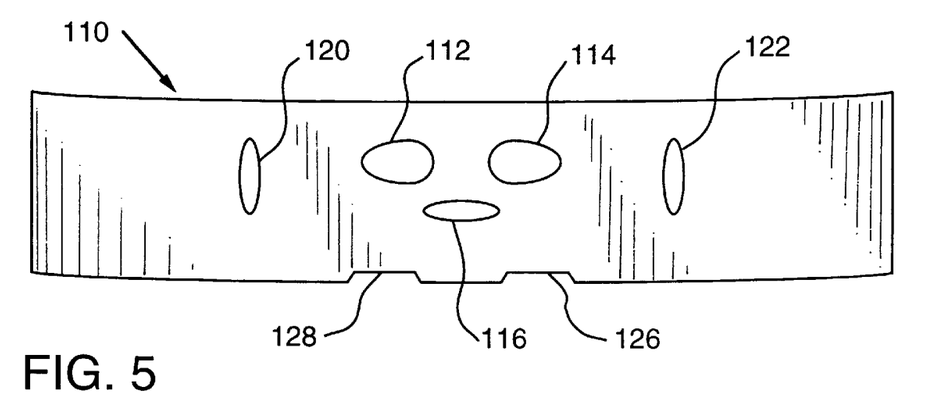
FIG. 5 is a sheet out of which a patient's restraining mask may be custom fabricated.

FIG. 5 shows a sheet 110 of suitable thermoplastic material having eye openings 112, 114, a nose and mouth opening 116 and ear openings 120, 122. A pair of recesses 126, 128 are formed in the thermoplastic sheet 110. This is a known prior art blank from which the mask 10 (FIG. 2) is formed so as to provide complimentary shape between the face of the particular patient and the overlying mask in order that intimate connection may be made with the underlying head support 8 (FIG. 2) in immobilizing the head. In conventional practices, the sheet 110 is heated to make it formable without melting the same and without providing excess heat to the face of a patient. It is then shaped so as to conform to the facial dimensions and shape of the patient to provide eye openings 112', 114', nose and mouth opening 116' and ear openings 120', 122'. The mask will be secured through tabs 140, 142 to the underlying head restraint in a manner to be described herein with reference to FIG. 7.

Figure 6:
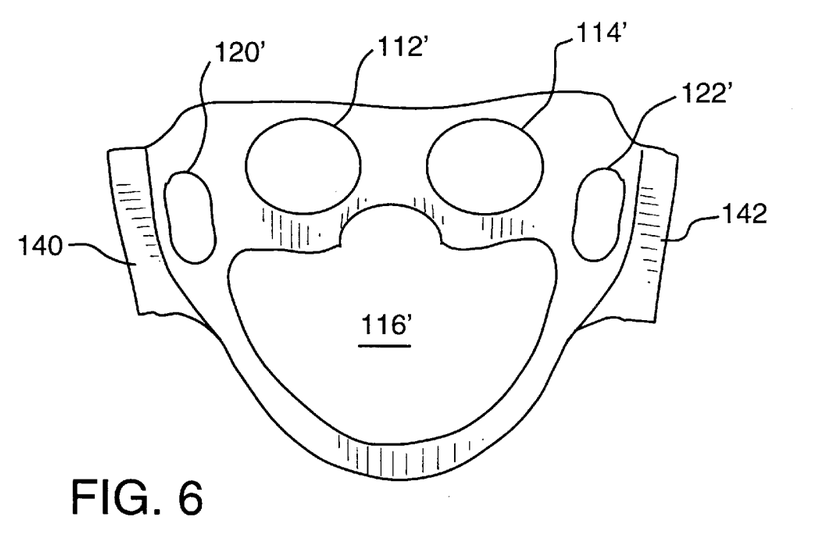
FIG. 6 shows an example of a fabricated patient restraining mask.
Figure 7:
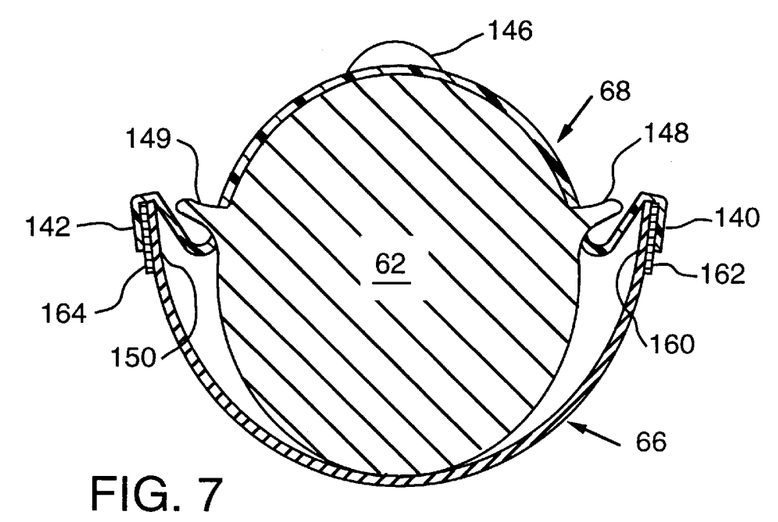
FIG. 7 is a cross-sectional illustration viewed from the rear through 7—7 of FIG. 4 showing a patient supported on a head support and having an overlying restraining mask.

FIG. 7 shows a cross-sectional illustration of the human head 62 supported on the head support 66 and restrained from above by mask 68. The patient's nose 146 and ears 148, 149 project through the mask. Referring to FIGS. 6 and 7, it will be seen that tabs 140, 142 of the lateral portions of the mask 68 are secured to the upper portions 150, 160 of the head support 66 by any suitable means so as to provide intimate securement of the head 62 between the head support 66 and mask 68. In the form shown, barb and loop means, 162, 164 in the form of an elongated strip which is preferable coextensive with the tabs 140, 142 are employed. The material sold under the trade designation may be employed for this purpose. This permits ease of securement in adjustable intimate relationship and ready removal at the end of the diagnostic or therapeutic medical procedure.

Figure 8:
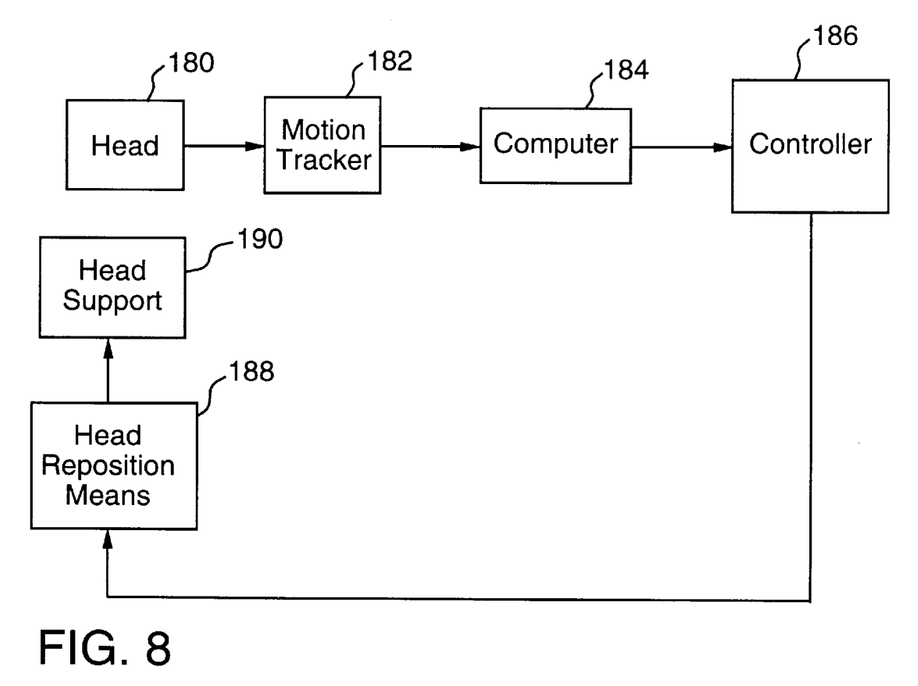
FIG. 8 is a schematic block diagram illustrating how the system of the present invention may be employed.

Referring to FIG. 8, a schematic illustration of the method and apparatus of the present invention will be considered. The head 180 positioned as shown in FIG. 7 is monitored during the medical procedure for movement by suitable known motion tracking systems 182 which, as shown in FIG. 1, monitors light reflecting from a reflector element secured to the patient's head with movement therewith. The reflected light is converted to electrical signals. A suitable optical tracking system for use in the present invention is the one sold under the trade designation Polaris by Northern Digital, Inc. of Waterloo, Ontario Canada. The signals generated during the motion tracking stage 182 will be receiving and processed within computer 184 which may be any suitable microprocessor or PC, for example. A comparison will be made between the signals representing the actual position of the head at a given instance in time and the desired position. To the extent that there has been a departure from the desired position and the departure exceeds a predetermined movement limit the computer issues a signal to controller 186 which will control the head repositioning means 188 and produce responsive movement of head support 180. If desired, the controller 186 may be part of the computer 94. The head positioning means 188, in a preferred embodiment, consists of a plurality of motors which facilitate movement in a translational manner in three directions along coordinate axes and three degrees of rotational movement therearound. The operation of one or more of the motors causes responsive controlled movement of the head support 190 on which the head 180 is secured thereby effecting restoration of the head to the desired position.

The present invention contemplates performing this cycle at a very rapid rate and effecting restoration of the head to the head 180 to the original position after very small departures from the desired position. Such departures will preferably be under 1 cm and most preferably under about 0.4 mm. The cycle of operation will begin with the computer initially determining the position of the patient's head with respect to the x, y, and z axes and the initial angular positions about the x, y and z axes. The computer 184 then repeats the calculations of head position at a high frequency on the order of about 10 to 30 Hz. This minimizes the amount of patient body portion movement between monitoring cycles. The head repositioning will preferably be performed at a high-frequency of greater than 10 Hz and generally within the range of about 10 to 30 Hz. Communication between the motion tracking system 182 and the computer 184 may be by any suitable software system as will be well known to those skilled in the art. A suitable such system is that sold under the trade designation LabVIEW by National Instruments Corporation.

The motors employed in head repositioning means 188 may be stepping motors which have the capability of moving at the rate of 1,500,000 per second which is more than adequate for purposes of the present invention. Limit switches (not shown) may be provided to protect the patient's head from excessive motion by the head support 180.

Figure 9:
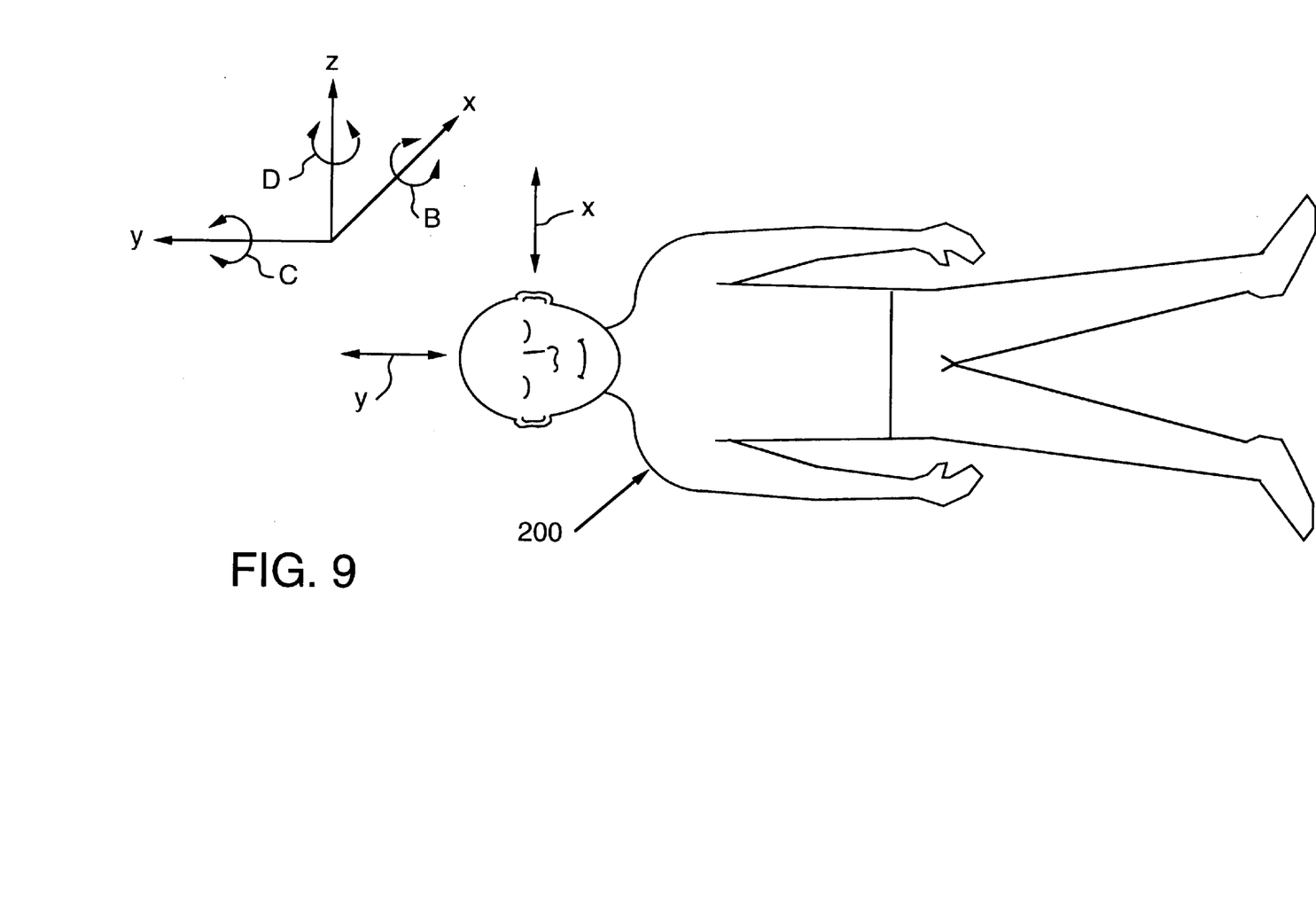
FIG. 9 shows a plan view of a patient with reference to the three axes of translation and three axes of rotation.

Referring to FIG. 9, there is shown a plan view of a patient 200 with respect to which the reference axes will be considered. For purposes of clarity of disclosure, the x axis will be shown as being oriented in a direction of translation which is lateral with respect to the y axis which is oriented in a generally head-to-toe direction. The z axis represents translation in a direction perpendicular to the page. Rotational movement is around each of the x, y, z axes is indicated by the double-headed arrows B, C, D, respectively. It will be appreciated that in both the translational movements and the rotational movements, in the preferred embodiment, movement will be effected in either translational or rotational direction.

Figure 10:
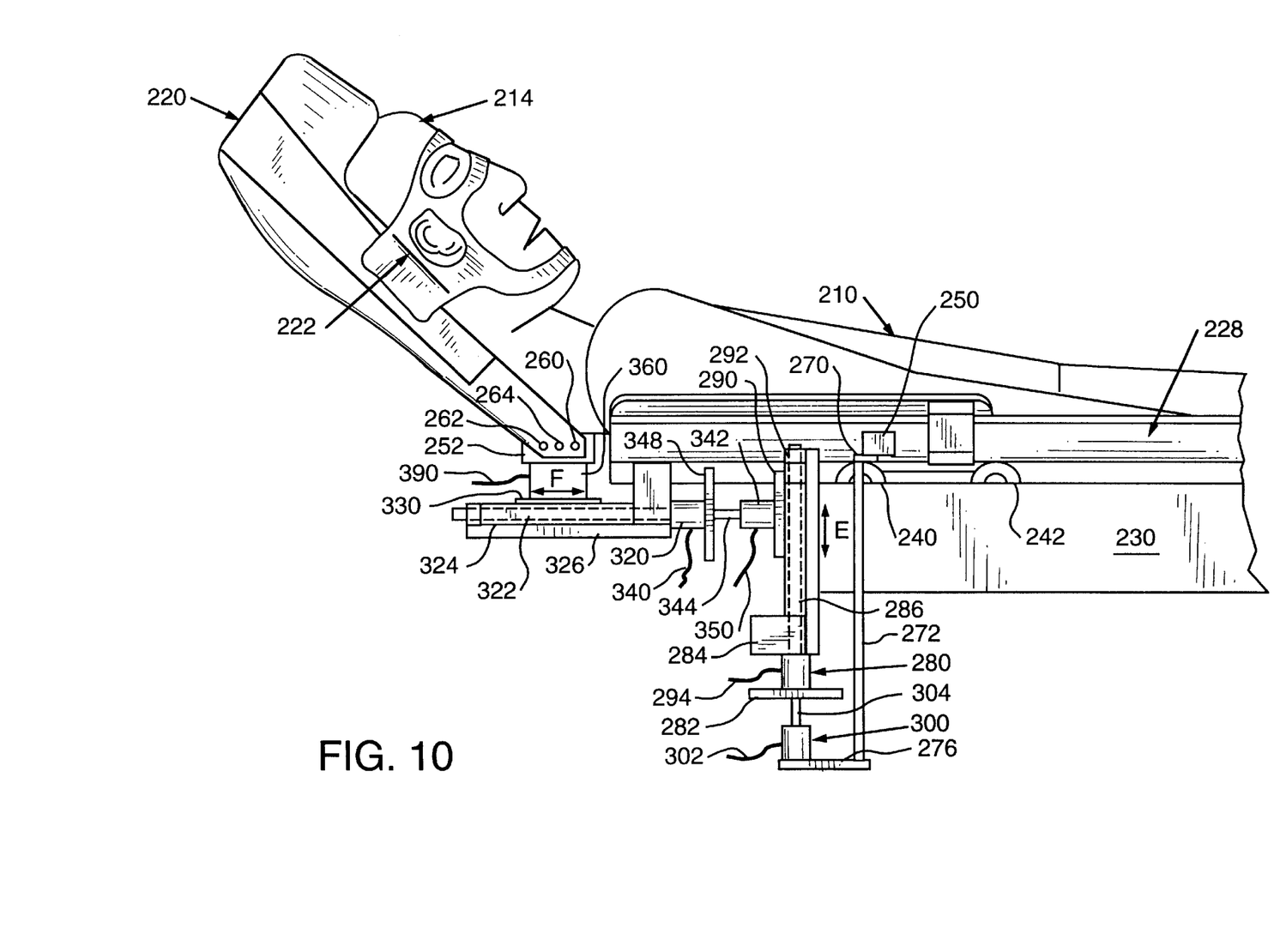
FIG. 10 is a front elevational view showing a patient with his head restrained and a portion of the head moving system of the present invention for effecting translation in a lateral, vertical or head-toe direction and associated apparatus for rotating the head about the translational axes.
Figure 11:
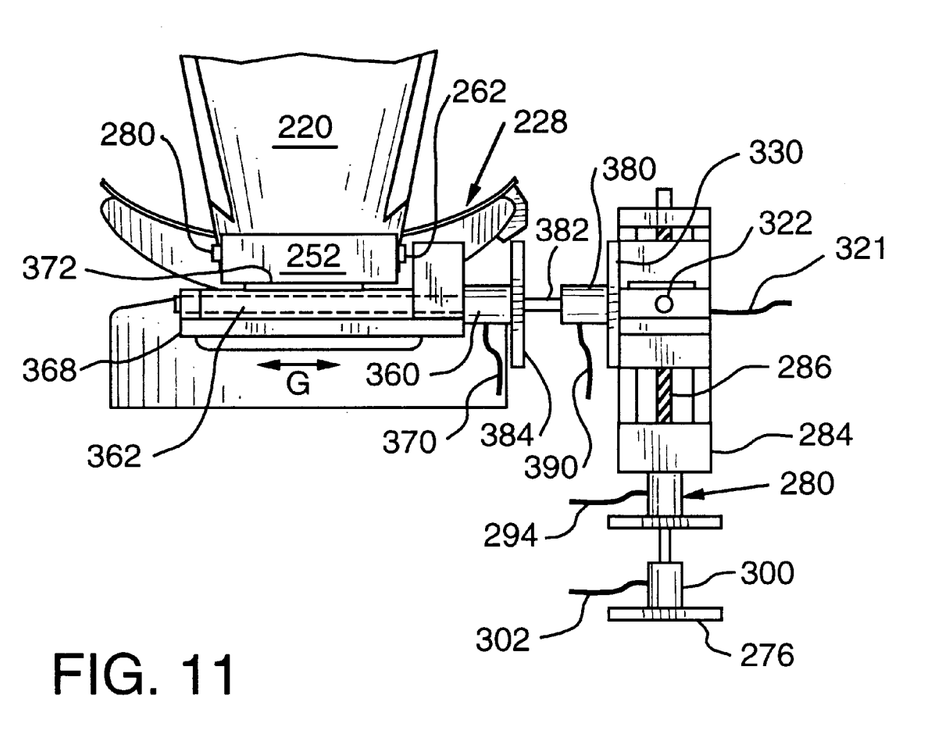
FIG. 11 is a rear elevational view of a portion of the apparatus of FIG. 10.

Referring now to FIGS. 10 and 11, details of the present invention will be considered. In general, it is contemplated that a motor will be provided to effect translational movement along three axes each of which is perpendicular to the other two axes as in x, y, z or orthogonal relationship. Three additional motors are provided to effect angular rotation about each of the three axes. All of the six degrees of movement are to, in the aggregate, restore the head support to its desired or original position. Both the rotational movement and the linear movement may be effected in either direction by each motor.

Referring to FIGS. 10 and 11, details of a preferred embodiment of the invention will be considered. A patient 210 has a head 214 secured between head support 220 and mask 222 so as to resist undesired movement of the head. The patient's body is supported on movable bed 228 which is subjected to movement along fixed underlying bed 230 by rollers, such as 240, 242 which move along a track in the fixed bed 232. The power means which effect the six degrees of movement of the head support 220 and will be described in greater detail hereinafter, are secured by anchor block 250 to movable bed 228 and by connecting member 252 to the lower portion of head support 220 by suitable means, such as bolts 260, 262, 264 which are provided as shown in FIG. 10 with corresponding nuts. It will be appreciated that any suitable means for securing anchor block 250 and connecting member 252 may be employed it being understood that the spacing between the movable bed 228 and the head support 220 will remain substantially constant as a result of the rigid connection through the power means.

Figure 12:
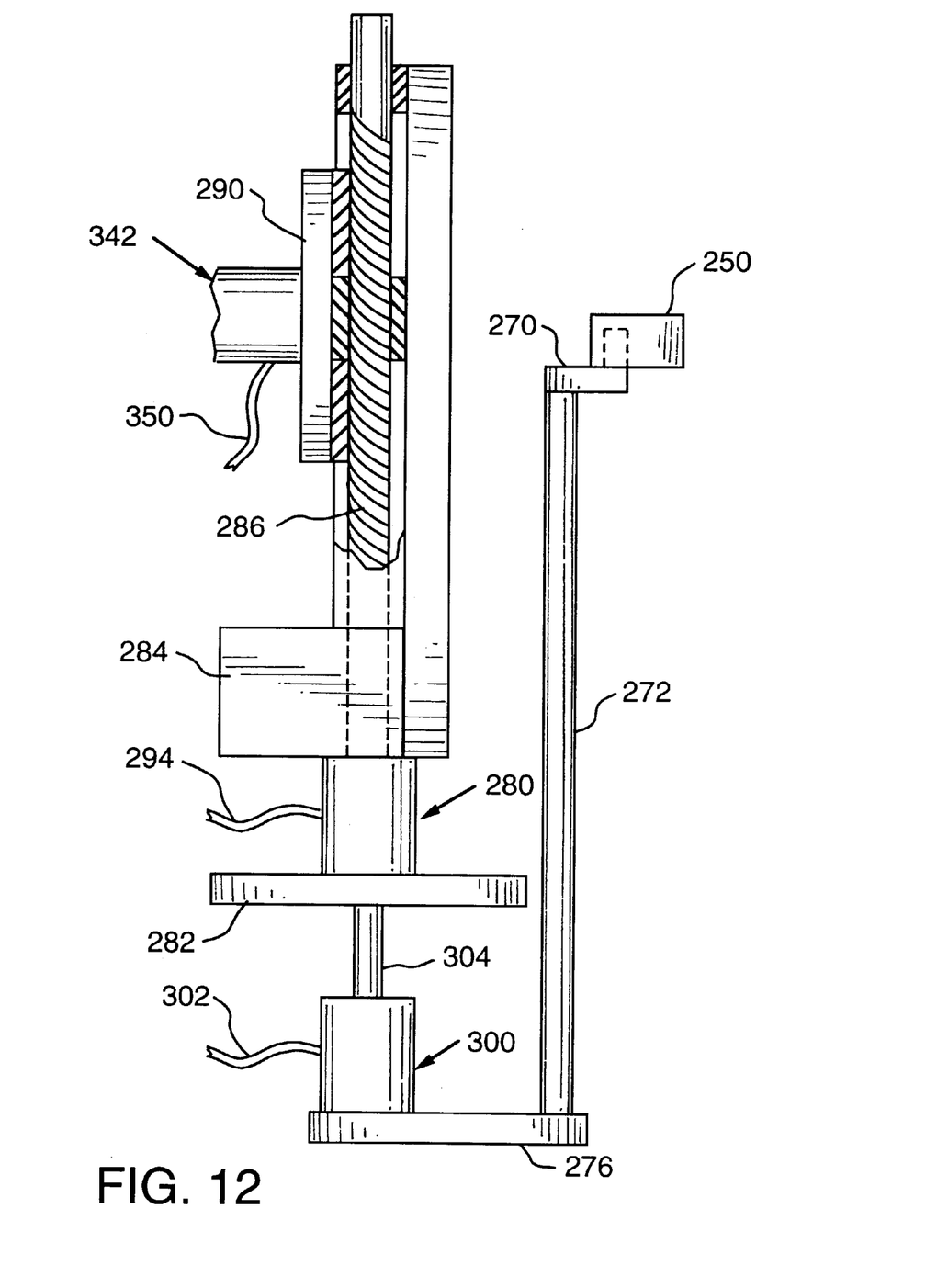
FIG. 12 shows an elevational view of a translational motor means and rotational motor means for translating the head in a vertical direction and rotating about the vertical axis as well as means for securing the motor assembly to the movable patient bed.

Referring first to FIGS. 10 and 12 and vertical translational movement, a rigid connection is made from anchor block 250 through connector block 270 and connecting rod 272 to motor support platform 276. Motor 280 is fixedly secured to support plate 282 and slide element 284. Rotation of the threaded output shaft 286 of motor 280 results in sliding movement in one of the two translational directions indicated by double-headed arrow E thereby causing movement in one of these two directions of plate 290. For convenience of reference herein, the slide element 290 and the associated threaded interior bore 292 which cooperates with motor output shaft 286 will collectively be referred to as part of the power means and be a "motor." A lead 294 which in the form of an electric motor may be an electrical connection which energizes and controls operation of the motor in the direction of rotation so as to determine in which translational direction E the slide plate 290 moves is provided. It will be understood that if the motor is hydraulic or pneumatic appropriate hydraulic or pneumatic lines and associated controls would be provided. Similarly, in the event that the output of a given motor cooperates with transmission means, such as speed reducing gears, for example, this too is contemplated.

It will be understood, therefore, that with reference to the present process, as shown schematically in FIG. 8, when it is determined that repositioning of the head includes an element of translation in the z direction, motor 280 will be activated with the direction of rotation and thereby the direction of sliding of plate 290 being determined along with the magnitude of movement. Motor 300 which may be energized and controlled by lead 302 has its output shaft 304 fixedly secured to plate 282 and its base fixedly secured to support plate 276. Whereas motor 280 effects translational movement along the z or vertical axis, rotation of output shaft 304 will cause rotation of the entire power means assembly about the z axis with rotation being effected in whichever rotational direction is desired.

In the preferred embodiment of the invention, similar systems will be provided for the x and y axes with their being a fixed connection among all three so that actuation of a single motor for correction in a single translational or rotational direction will effect the proper movement of the head support 200. With the high frequency of scanning contemplated by the present invention, it will be appreciated that one of the objectives is to effect corrective action after only a small amount of movement has occurred. Such movement may be on the order of about 0.2 to 0.4 mm, for example.

Figure 13:
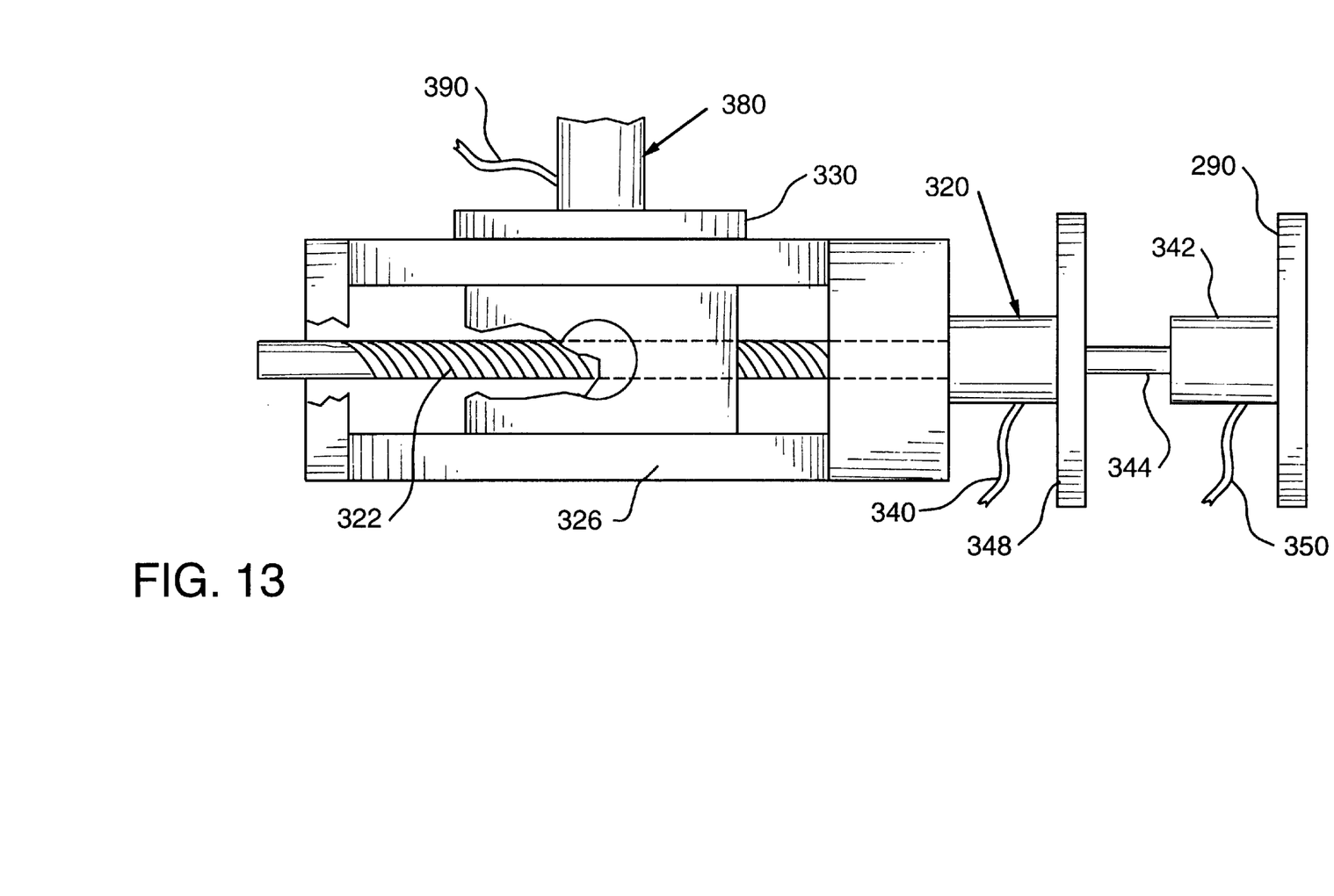
FIG. 13 is a top plan view similar to FIG. 12 showing motor means for effecting translational movement in the head-toe direction and rotational movement thereabout.

Referring to FIGS. 10 and 13, the horizontally oriented segment of the power means which will be responsible for translational movement in either direction along the head-to-toe or y axis and rotational movement in either direction about the y axis will be considered. Motor 320 has a threaded output shaft 322 which is engaged with a threaded sleeve 324 of slide element 326 which has a plate 330 fixedly secured thereto. Lead 340 energizes and controls operation of the translational motor. Motor 342 has its output shaft 344 fixedly secured to plate 348 which is fixedly secured to motor 320. Slide element 290 is fixedly secured to the base of motor 342 and control and energizing lead 350 is provided therefor. In this manner, operation of motor 320 will cause translational movement of slide plate 330 in either translational direction F along the head-to-toe or y axis and rotation of motor 342 will cause rotation about the same axis.

Figure 14:
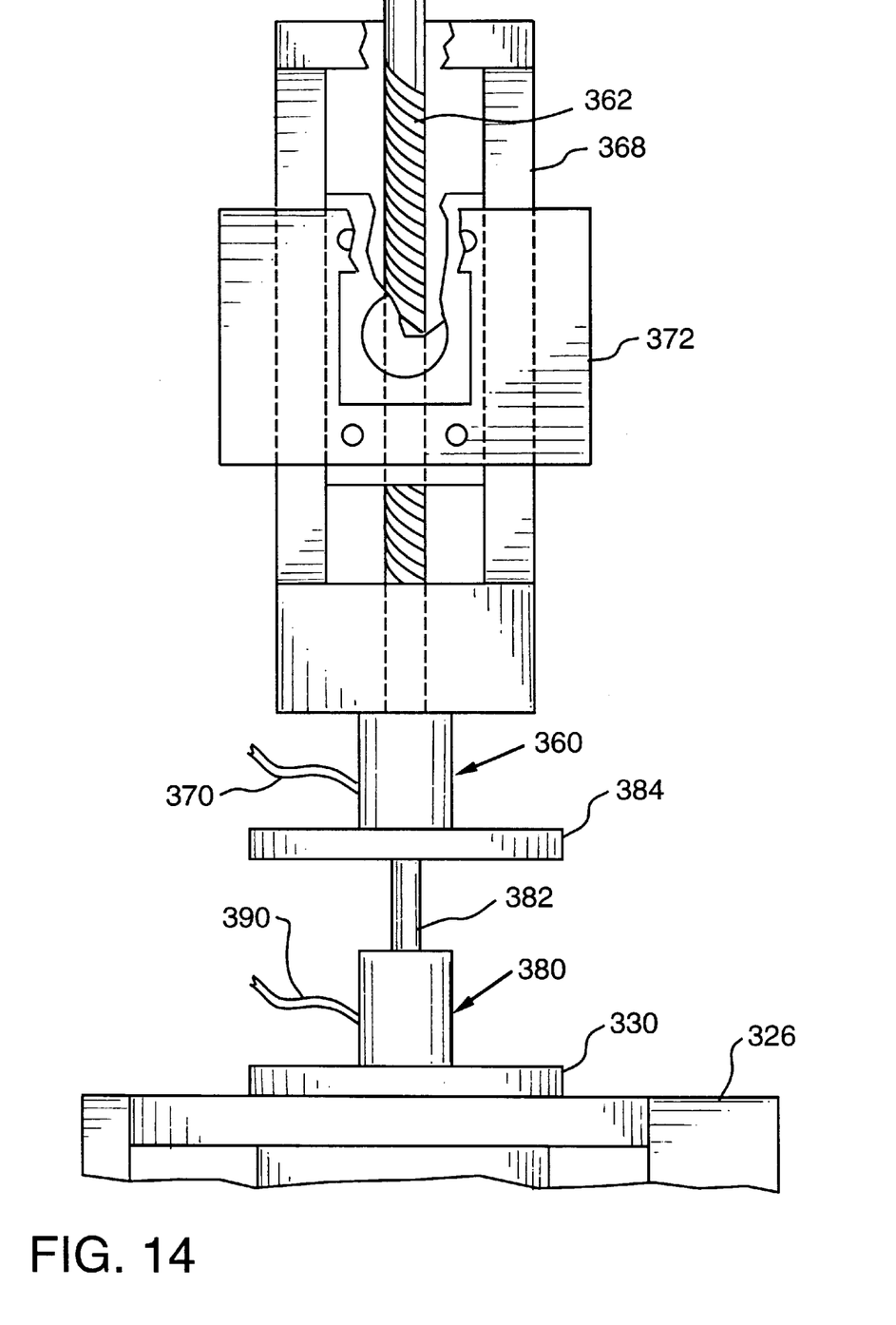
FIG. 14 is a top plan view showing a form of translational motor means and rotational motor means for moving the patient's head in a lateral direction.

Referring to FIGS. 11 and 14 the horizontally oriented motor portion which will effect movement in a translational direction along the direction indicated by the letter G along the x axis or laterally with respect to the patient will be considered. Motor 360 has a threaded output shaft 362 which cooperates with threaded bore in slide element 368 which is connected to overlying support block 252 through block 372. Lead 370 energizes and controls this motor. Rotational motor 380 has its base fixedly secured to slide member 330 and an output shaft 382 which is fixedly secured to plate 384 which, in turn, is fixedly secured to motor 360. Lead 390 energizes and controls this motor 380.

It will be appreciated, therefore, that energizing at least one of the six motors 280, 300, 320, 342, 360, 380 will effect movement of the head support 220 and the head to thereby facilitate accurate repositioning of the head to the desired position which, in most instances, will be the original position.

It will be appreciated that appropriate clearance with respect to other portions of the apparatus will be provided so as to permit the contemplated degree of translational and rotational movement and that limit switches (not shown) will be provided so as to avoid excessive travel. The six motors may all be operated simultaneously.

Figure 15:
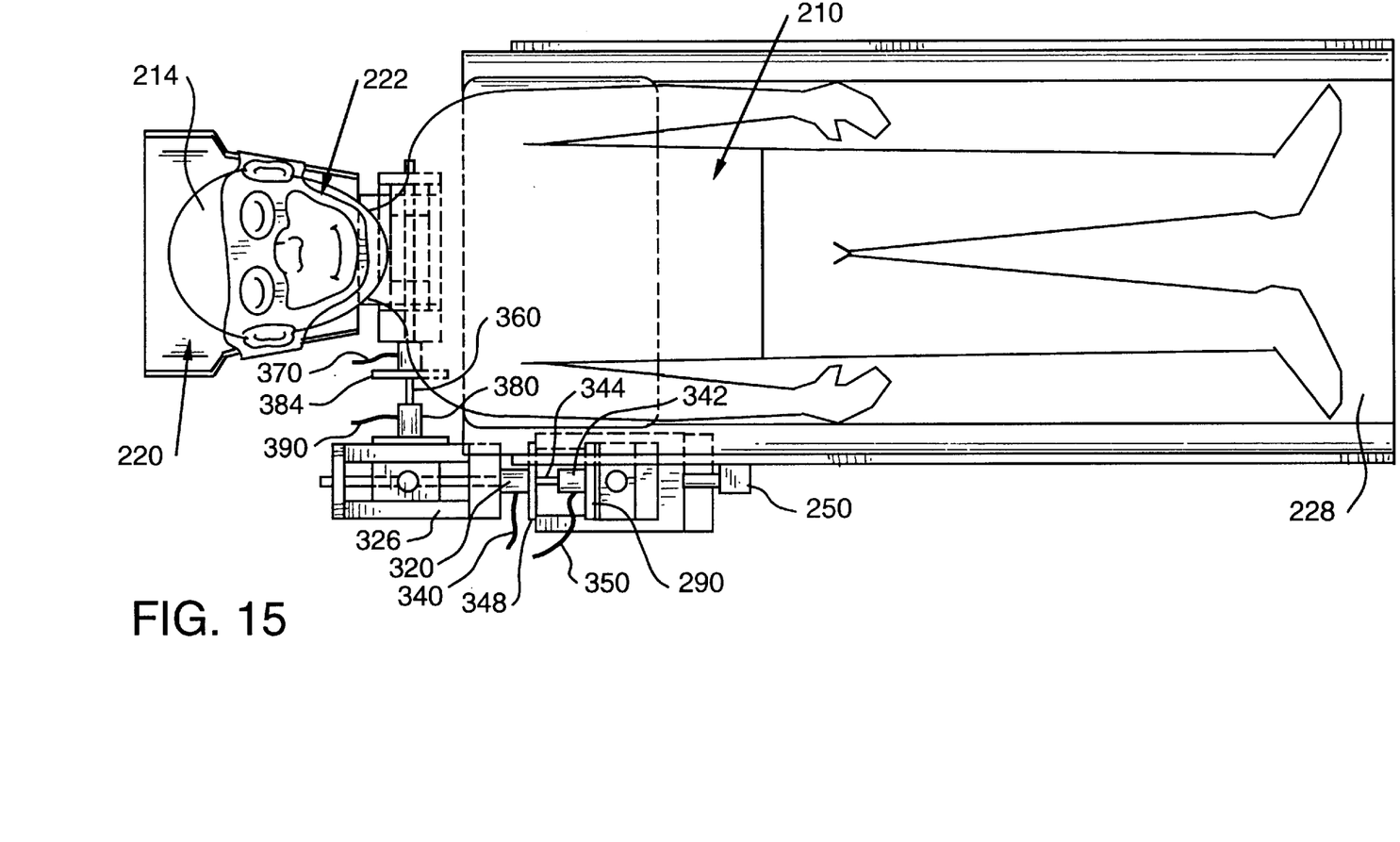
FIG. 15 is a top plan view showing the patient and the two horizontally oriented portions of the system for translational and rotational means.

Referring to FIG. 15, a plan view showing the patient 210 having his body supported on the movable portion of the bed 228 and head 214 supported on head support 220 with the overlying mask 222.

It will be appreciated, therefore, that the present invention has provided an apparatus and an associated method for monitoring undesired body movement during a medical procedure and rapidly restoring the body portion to the desired or original position. While particular emphasis has been placed herein on a preferred use with the head for medical procedures, such as a brain scan, it will be appreciated that the invention is not so limited and it may be employed with other portions of the body by providing the patient motion monitoring coupled with power means, such as the six motors disclosed herein, to restored the position after relatively small travel has occurred. This is accomplished through the use of high frequency monitoring which may be greater than 10 Hz and restoration of the body portion to its original position after movement of less than 1 cm.

The apparatus may be employed with a wide variety of imaging, such as PET or MRI, for example, and radiotherapy, such as stereotactic radiosurgery, for example.

While prime emphasis has been placed on the use of the apparatus and method, for medical purposes, the invention is not so limited and may be employed for inspection of inanimate objects in manufacturing and other environments and the definition of "medical procedure" includes such uses.

Whereas particular embodiments of the invention have been described herein for purposes of illustration, it will be evident to those skilled in the art that numerous variations of the details may be made without departing from the invention as defined in the appended claims.

What is claimed is:

1. Apparatus for positioning a patient in a desired position during a medical procedure, the patient having a body including a head and a face said apparatus including means for restraining the portion of the patient's body being subjected to said medical procedure, tracking means for tracking motion of said body portion, computer means for receiving signals from said tracking means and determining if said body portion has moved from the desired position and if it has emitting a corrective signal, and power means for receiving said computer means corrective signals and responsively moving said body portion to the desired position, said power means being capable of moving said body portion in both translational and rotational directions, said means for restraining including means for restraining the patient's head, said means for restraining the patient's head having a head support portion for underlying support of the patient's head and a mask for overlying the patient's face, and mask securing means for securing said head support and said mask with a patient's head positioned therebetween, said power means including motor means operatively associated with said head support for moving said head support to the desired position, said motor means including (a) a first motor for moving said head support in a first translational direction (b) a second motor for moving said head support in a second translational direction generally perpendicular to said first translational direction, and (c) a third motor for moving said head support in a third translational direction generally perpendicular to said first and second translational directions, and said motor means also including (a) a fourth motor for effecting rotary movement of said head restraint about said first translational direction, (b) a fifth motor for effecting rotary movement of said head support about said second translational direction, and (c) a sixth motor for effecting rotary movement of said head support about said third translational direction.

2. The patient positioning apparatus of claim 1 including said first motor being mounted for rotational movement with said fourth motor, said second motor being mounted for rotational movement with said fifth motor, and said third motor being mounted for rotational movement with said sixth motor.

3. The patient positioning apparatus of claim 1 including said six motors providing a head support moving assembly, and said head support moving assembly being structured to have one portion secured to said head support and a second portion secured to a patient supporting bed.

4. The patient positioning apparatus of claim 1 including said computer means being capable of determining at a frequency of about 10 to 30 Hz if the body portion has moved from the desired position.

5. The patient positioning apparatus of claim 1 including imaging means for performing said medical procedure.

6. The patient positioning apparatus of claim 5 including said imaging means including apparatus for positron emission tomography.

7. The patient positioning apparatus of claim 1 including radiotherapy apparatus for performing said medical procedure.

8. The patient positioning apparatus of claim 1 including said motors being slide motors.

9. The patient positioning apparatus of claim 1 including said motors being stepping motors.

10. Apparatus for positioning a patient in a desired position during a medical procedure, the patient having a body, the body including a head and a face, said apparatus including means for restraining the portion of the patient's body being subjected to said medical procedure, tracking means for tracking motion of said body portion, computer means for receiving signals from said tracking means and determining if said body portion has moved from the desired position and if it has emitted a corrective signal, power means for receiving said computer means corrective signals and responsively moving said body portion to the desired position, said means for restraining including means for restraining the patient's head, said means for restraining the patient's head having a head support portion for underlying support of the patient's head, a mask for overlying the patient's face, and mask securing means for securing said head support and said mask with the patient's head positioned therebetween, said power means including motor means operatively associated with said head support for moving said head support to the desired position;

said motor means including a first motor for moving said head support in a first translational direction, a second motor for moving said head support in a second translational direction generally perpendicular to said first translational direction, and a third motor for moving said head support in a third translational direction generally perpendicular to said first and second translational directions, said motor means also including a fourth motor for effecting rotary movement of said head restraint about said first translational direction, a fifth motor for effecting rotary movement of said head support about said second translational direction, and a sixth motor for effecting rotary movement of said head support about said third translational direction, said first motor being mounted for rotational movement with said fourth motor, said second motor being mounted for rotational movement with said fifth motor, said third motor being mounted for rotational movement with said sixth motor, said first motor and said fourth motor having output shafts oriented generally parallel to said first translational direction, said second motor and said fifth motor having output shafts oriented generally parallel to said second translational direction, and said third motor and said sixth motor having output shafts oriented generally parallel to said third translational direction.

11. The patient positioning of claim 10 including each said pair of motors oriented parallel to a said translational direction being directly or indirectly connected mechanically to the other two said pairs of motors.

12. A method for positioning a patient in a desired position during a medical procedure, the patient having a body with a head, the head having a face and an undersurface, said method including providing tracking means for tracking motion of a portion of said patient's body, computer means for emitting a signal when said patient body portion is not in the desired position and responsive power means for moving said patient body portion to the desired position when said computer means emits a said signal to said power means, said power means being capable of moving the patient body portion in both translational and rotational directions, restraining the portion of said patient's body which is being subjected to said medical procedure, tracking motion of said body portion, employing a plurality of motors which form a part of said power means to move said body portion to the desired position responsive to said signals from said computer means, and employing a combination of at least one of the following in effecting said corrective movement: (a) translation of the patient's head in at least one of three translational directions and (b) rotation of said patient's head in at least one of three rotational directions.

13. The patient positioning method of claim 12 including employing said method to position a patient's head as said body portion.

14. The patient positioning method of claim 13 in which the patient's head has a position during said medical procedure, and including employing optical tracking means to track the position of said patient's head and emit corresponding position signals to said computer means.

15. The patient positioning method of claim 14 including performing said step of employing a plurality of motors when said head has moved less than 1 cm.

16. The patient positioning method of claim 13 including employing a combination of translation and rotation to position said patient's head.

17. The patient positioning method of claim 12 including providing head restraint means which includes a head support for supporting the undersurface of a patient's head and a mask for overlying the patient's face, securing said patient's head between said head support and said mask, initiating said medical procedure, and tracking motion of said patient's head during said medical procedure and effecting correction of said patient's head position if undesired head movement occurs.

18. The patient positioning method of claim 17 including the step of performing diagnostic imaging.

19. The patient positioning method of claim 17 including the step of performing radiotherapy treatment.

20. The patient positioning method of claim 17 including performing the step of determining the head position at a frequency in excess of 10 Hz.

21. The patient positioning method of claim 17 including employing said method in brain imaging by positron emission tomography.

22. The patient positioning method of claim 17 in which said patient's head has an original position during said medical procedure and further including the step of returning the patient's head to the original position.

23. The patient positioning method of claim 22 including employing said method in functional brain imaging.

24. The patient positioning method of claim 12 in which the patient's body portion is the patient's head, the patient's head having an original head position during said medical procedure, and including the step of effecting return of the patient's head to the original head position.

25. The patient positioning method of claim 12 including employing a first said motor to translate said head in a first linear direction, employing a second said motor to translate said head in a second linear direction which is generally perpendicular to said first linear direction, and employing a third said motor to translate said head in a third linear direction which is generally perpendicular to said first and second linear direction.

26. A method for positioning a patient in a desired position during a medical procedure, the patient having a body with a head, the head having a face and an undersurface, said method including providing tracking means for tracking motion of a portion of said patient's body, computer means for emitting a signal when said patient body portion is not in the desired position and responsive power means for moving said patient body portion to the desired position when said computer means emits a said signal to said power means, said power means being capable of moving the patient body portion in both translational and rotational directions, restraining the portion of said patient's body which is being subjected to said medical procedure, tracking motion of said body portion, employing a plurality of motors which form a part of said power means to move said body portion to the desired position responsive to said signals from said computer means, employing a first said motor to translate said head in a first linear direction, employing a second said motor to translate said head in a second linear direction which is generally perpendicular to said first linear direction, employing a third said motor to translate said head in a third linear direction which is generally perpendicular to said first and second linear direction, employing a fourth said motor to rotate said head about said first linear direction, employing a fifth said motor to rotate said head about said second linear direction, and employing a sixth said motor to rotate said head about said third linear direction.

* * * * *